(12) United States Patent
Fukuoka et al.

(10) Patent No.: US 7,374,873 B2
(45) Date of Patent: May 20, 2008

(54) ANALYSIS METHOD FOR SUBSTANCE

(76) Inventors: Takao Fukuoka, 68-17, Terada Ichinokubo, Joyo-shi, Kyoto 610-0121 (JP); Keitaro Nakamura, 23-10, Yatayamacho, Yamatokoriyama-shi, Nara 639-1055 (JP); Yasushige Mori, 1-64, Todo Aramaki, Uji-shi, Kyoto 611-0013 (JP)

(*) Notice: Subject to any disclaimer, the term of this patent is extended or adjusted under 35 U.S.C. 154(b) by 0 days.

(21) Appl. No.: 11/716,553

(22) Filed: Mar. 12, 2007

(65) Prior Publication Data
US 2007/0275482 A1    Nov. 29, 2007

Related U.S. Application Data

(62) Division of application No. 10/469,932, filed as application No. PCT/JP01/01854 on Mar. 9, 2001, now Pat. No. 7,198,957.

(51) Int. Cl.
*G01N 33/551* (2006.01)
(52) U.S. Cl. .................. 435/4; 436/524; 436/525
(58) Field of Classification Search .................. 435/4; 436/524, 525
See application file for complete search history.

(56) References Cited

FOREIGN PATENT DOCUMENTS

| JP | 9-70527 | 3/1997 |
|---|---|---|
| JP | 11-61209 | 5/1999 |

OTHER PUBLICATIONS

Keitaro Nakamura et al., "Preparation of Gold-Clay Coexisting Gel and its Properties of Surface-enhanced Raman Scattering," The autumnal workshop proceedings 1999 of the Society of Powder Technology, Japan, 44 (1999).

Keitaro Nakamura et al., "The Preparation of the Gold and Clay Coexisting Gel and its Properties of Surface-enhanced Raman Scattering," (English translation of "Kin . Nendo Kyouzon Gel tai No Chousei to Hyomen Zoukyou Raman Sanran Tokusei"), The autumnal workshop proceedings 2000 of the Society of Powder Technology, Japan, pp. 44-46 (2000).

Chang, R. et al., "Surface Enhanced Raman Scattering," Plenum Press, New York and London, pp. 109, 126-127 (1982).

Kneipp, K. et al., "Surface-enhanced Raman scattering: a new tool for biomedical spectroscopy," Current Science, vol. 77, No. 7, pp. 915-924 (1999).

Kneipp, K. et al., "Extremely Large Enhancement Factors in Surface-Enhanced Raman Scattering for Molecules in Colloidal Gold Clusters," Soc. for Applied Spectroscopy, vol. 52, No. 12, pp. 1493-1497 (1998).

Hayat, M.A., "Colloidal Gold—Principles, Methods, and Applications [Methods for Synthesis of Colloidal Gold by Dean A. Handley]," Academic Press, Inc., San Diego, California, pp. 13-32 (1989).

Khlebtsov, N. et al., "Spectral Extinction of Colloidal Gold and its Biospecific Conjugates," Journal of Colloid and Interface Science, vol. 180, Article 0323, pp. 436-445 (1996).

Akbarian, F. et al., "Porous Sol-Gel Silicates Containing Gold Particles as Matrices for Surface-Enhanced Raman Spectroscopy," Journal of Raman Spectroscopy, vol. 27, pp. 775-783 (1996).

*Primary Examiner*—Christopher L. Chin
(74) *Attorney, Agent, or Firm*—Finnegan, Henderson, Farabow, Garrett & Dunner, L.L.P.

(57) ABSTRACT

A method for analyzing a substance, comprising: a step of obtaining a dispersion complex by co-existing fine particles having a dispersion property higher than that of lyophobic fine particles in a dispersion phase of the lyophobic fine particles at a concentration sufficient for covering a periphery of a lyophobic fine particle group; a step of contacting the dispersion complex and a fluid containing an analyte; and a step of analyzing the analyte using an optical measuring means, wherein the lyophobic fine particles exist in the dispersion phase in a group for providing the surface enhancing effect. The method is effective for analysis of a slight amount substance or a low concentration substance.

6 Claims, 7 Drawing Sheets

— containing the montmorillonite:
  immediately after the preparation
--- containing the montmorillonite: after one minute
······ containing the montmorillonite: after 20 days
—·— without the montmorillonite:
  immediately after the preparation
—··— without the montmorillonite: after 20 days

① aggregation state B: passage of one day
② without the synthetic smectite: passage of one day

ANALYSIS METHOD FOR SUBSTANCE

RELATED APPLICATIONS

This application is a divisional of application Ser. No. 10/469,932 filed Sep. 5, 2003, now U.S. Pat. No. 7,198,957 which is a §371 of International Application No. PCT/JP01/01854, filed Mar. 9, 2001.

TECHNICAL FIELD

The present invention relates to all the analysis method utilizing the surface enhancing effect in a vibration spectroscopy method. In particular, it relates to the life science field, which requires analysis of an organism component, such as the function analysis of a protein in an aqueous solution, and furthermore, the earth, environment field, which requires analysis of a hazardous substance in the environment, or the like.

BACKGROUND TECHNOLOGY

Clarification of the physiological function of the bio functional substances, such as a protein and a nucleic acid has been an important task. In addition thereto, control and design of the physical chemical properties are indispensable for realization of a bioreactor, a biosensor, a DNA chip, and for the near further, a bio element, or the like. Therefore, development of the analysis methods for the physical chemical properties of the bio functional substances and analysis reagents for the measurement is expected.

A bio functional substance has the activity in an organism, and the organism has water as a medium. Therefore, clarification of the physical chemical properties should be carried out in an aqueous solution. As an analysis method effective for examining the structure of a bio functional substance and the interaction with the substrate molecules in water, the Raman spectroscopy as a kind of the vibration spectroscopy method has been provided.

However, since the signal intensity obtained by the ordinary Raman spectroscopy is extremely low and the sensitivity is poor, a specimen concentration of several % or more has been required. Therefore, in the case of a bio functional substance, a specimen condensing operation is necessary and indispensable so that problems are involved in the cost, and the risk of losing or denaturation of the specimen during the operation.

In contrast, even in the case of the Raman spectroscopy, if a specimen interacts with metal fine particles, the surface enhancing effect of amplifying the signal intensity is known ("Surface enhanced Raman Scattering", ed. By R. K. Chang and T. E. Furtak, (Plenum Publishing; N.Y., 1982)). The enhancing sensitivity is said to be in general from 10,000 times to 1,000,000 times.

The surface enhancing effect appears dramatically in the case the above-mentioned metal fine particles are used in an aggregated state. A measuring method utilizing the surface enhancing effect is important also as a study method for the biotechnology (K. Kneipp, H. Kneipp, I. Itzkan, R. R. Dasari, and M. S. Feld, Biomedical Applications of Lasers, 77 (7), 915-924 (1999); Surface-enhanced Raman scattering: A new tool for biomedical spectroscopy).

According to a recent experiment using aggregation of precious metal fine particles, the surface enhancing effect reaching as much as 100,000,000,000,000 times capable of one molecule detection has been confirmed (K. Kneipp, H. Kneipp, R. Manoharan, E. Hanlon, I. Itzkan, R. R. Dasari, and M. S. Feld, Applied Spectroscopy, 52 (12), 1493-1497 (1998); Extremely large enhancement factors in surface-enhanced Raman scattering for molecules on colloidal gold clusters). Such metal fine particles are referred to as the substrate of the surface enhancing effect. Semiconductors such as a gallium and a gallium arsenide can also be the substrate.

As embodiments at the time of using metal fine particles as the substrate for the surface enhancing effect, a colloid of metal fine particles, a film with metal fine particles deposited on the surface in an island-like form, a glass matrix with metal fine particles dispersed in the inside by a sol gel method, a polymer matrix with metal fine particles dispersed in the inside, or the like has been reported so far. Moreover, the present inventors have also disclosed in the official gazette of the Japanese Patent Application Laid Open (JP-A) No. 11-61209 a technique for obtaining a stable dispersion of the precious metal fine particles by producing precious metal fine particles by the reducing reaction in a dispersion with plate-like fine particles of a swellable layered silicate, or the like dispersed.

Among the substrates, a colloid of nano precious metal fine particles in an aqueous solution is regarded as most convenience in the practical use. As the reason therefor, advantages such as 1) capability of synthesizing fine particles in a liquid phase method, and facilitation of handling, 2) adoptability to a continuous flow analysis system, 3) capability of controlling the particle size and the shape, 4) capability of easily defining the surface area, and 5) capability of changing the morphology for the theoretical analysis, have been pointed out (M. Kerker, D. S. Wang, H. Chew. O. Siiman, and L. A. Bumm, "Surface Enhanced Raman Scattering", ed. by R. K. Chang and T. E. Furtak, (Plenum Publishing, N.Y., 1982), pp. 109-128; Enhanced Raman scattering by molecules adsorbed at the surface of colloidal particles).

In any case, in order to use metal fine particles as the substrate for the surface enhancing effect, the dispersion state should be maintained stably. Conventionally, as the method for controlling the dispersion state, since the metal fine particles are lyophobic fine particles, 1) addition of a stabilizing agent in a liquid phase, 2) deposition onto a solid phase (including coating), 3) containment into a matrix of the above-mentioned glass, polymer, or the like, 4) coexistence of a swellable layered silicate with metal fine particles as mentioned in the above-mentioned official gazette of the Japanese Patent Application Laid Open (JP-A) No. 11-61209, or the like have been proposed.

Among these controlling methods, as a stabilizing agent to be used in a liquid phase, a surfactant such as a sodium dodecyl sulfate, a polyvinyl alcohol, a polyvinyl pyridine, a polyethylene glycol, an N-vinyl pyrrolidone, a bovine serum albumin, a γ-globulin, and a protective colloid such as a gelatin are known. Moreover, the "method for preventing colloid aggregation" of the Japanese Patent Application Laid Open (JP-A) No. 09-070527 discloses the stabilizing effect of a buffer agent such as a tris(hydroxymethyl)amino methane, or the like.

Moreover, as the deposit onto a solid phase, a method of depositing fine particles on a glass plate and stopping aggregation at a stage of a certain degree is frequently used. According thereto, it is possible to deposit the nano fine particles synthesized by the liquid phase method on the glass plate, thereby producing aggregations with different sizes and morphologies.

However, even if a stabilizing agent is used, it has been extremely difficult to maintain the aggregation state in the liquid without precipitation while maintaining the function of the fine particles in the dispersion phase of the lyophobic fine particles with a liquid used as the dispersion medium such as a colloid of precious metal fine particles in an aqueous solution. As a result, the reproductivity and the stability of a production method for a substrate of the surface enhancing effect dependent on the aggregation state of the lyophobic fine particles have been poor, and the performance is still insufficient.

Moreover, since the conventional stabilizing agent prevents aggregation by restraining approach of the fine particles with each other by adhering on the surface of the fine particles, the surface activity, which is an important function of the metal fine particles, is lost. Even in the case the metal fine particles are deposited on the solid phase, the dispersion and the deviation of the aggregation size distribution are large so that the reproductivity of the production method is poor, and furthermore, it is instable, and thus the stability can be maintained for about several days at most even if they are coated with an organic monomolecular layer such as a thiol. According to the containment in a matrix, loss of the surface activity of the metal fine particles by the matrix, and deterioration of the substance moving rate in the matrix are generated so that a substrate with the excellent surface enhancing effect cannot be obtained. The technique disclosed in the official gazette of the Japanese Patent Application Laid Open (JP-A) No. 11-61209 produces metal fine particles in a dispersion with plate-like fine particles dispersed so that a long time is required for the production of the metal fine particles, resulting in rise of the cost, and furthermore, since an acetone dicarboxylic acid, which can easily be decomposed, is used as the reducing agent, it is inconvenient in terms of handling.

That is, a substrate with the surface enhancing effect, being stable for a long time, capable of providing a quick response, to be produced with a good productivity while maintaining a high surface activity of the lyophobic fine particles, has not been known so far.

Therefore, an object of the present invention is to provide an analysis method of keeping lyophobic fine particles existing in a group as aggregation to be a dispersed phase, and using the obtained dispersion complex as the practical substrate of the surface enhancing effect.

DISCLOSURE OF THE INVENTION

In order to achieve the above-mentioned object, an analysis method of the present invention has the following characteristics. That is, a dispersion complex is obtained by co-existing fine particles having a dispersion property higher than that of the lyophobic fine particles (hereinafter referred to as the "dispersible fine particles"), in a dispersion phase of lyophobic fine particles existing in a group, at a concentration sufficient for covering the periphery of the lyophobic fine particle group. The dispersion complex accordingly obtained is used as the substrate of the surface enhancing effect. Then, the dispersion complex and a fluid containing an analyte are contacted for measuring the concentration of the analyte or the nature by an optical measuring means while utilizing the surface enhancing effect obtained by the approach of the analyte to the lyophobic fine particle group.

According to the present invention, since the group state of the lyophobic fine particles can be maintained by the dispersible fine particles, excessive progress of the aggregation and generation of the precipitation can be restrained. As a result, the performance as the substrate of the surface enhancing effect can be maintained over a long time so that analysis using the surface enhancing effect can be carried out easily.

DETAILED DISCLOSURE OF THE INVENTION

A dispersion complex is produced in general by a method comprising the following steps (a) to (d) in the present invention.

(a) A step of dispersing lyophobic fine particles in a liquid phase.

(b) A step of starting aggregation by adding an aggregating agent, or the like, for obtaining a group of the lyophobic fine particles.

(c) A step of adding dispersible fine particles so as to obtain a concentration sufficient for covering the periphery of the lyophobic fine particle group to the liquid phase after the step (b).

(d) A step of collecting the obtained group of the lyophobic fine particles as a dispersion complex.

As the lyophobic fine particles, although they are not particularly limited, metal fine particles containing as the main component at least one selected from the group consisting of gold, silver, copper, platinum, nickel, indium and palladium, which has a 1 to 100 nm particle size close to the atom size, or semiconductor fine particles of gallium or gallium arsenide, or the like can be used. However, it is not limited thereto, and any fine particles capable of providing a function different from the bulk can be used.

The lyophobic fine particles are not particularly limited, and they can be provided to the above-mentioned (b) step as they are after synthesis by a liquid phase method. Moreover, by adding and agitating fine particles obtained by another method in a liquid, they may be dispersed in the liquid phase.

The method for starting the aggregation and obtaining the lyophobic fine particle group is not particularly limited, and one or more of the following five means can be selected: (1) increase of the particle concentration, (2) the ionic strength rise by addition of an electrolyte, which brings about the salting out phenomenon, such as a sodium chloride and an aluminum sulfate, (3) cross linking by a polymer, (4) the temperature rise, and (5) decrease of the polarity of the dispersion medium.

The stability of the fine particle dispersion phase in the liquid can be explained by the DLVO theory. A explanation of an example of gold fine particles by the DLVO theory will be provided hereafter, and the other lyophobic fine particles can be explained in the same manner. Gold fine particles, which have been reduced chemically, adsorb a reducing agent anion or a complex metal anion, thereby being charged negatively (M. A. Hayat Ed. "Colloidal gold" vol. 1 and vol. 2, Academic Press Inc., 1984). In the case the relative size balance between the electrostatic repulsion potential and the attraction potential dependent on the Van Der Waals force, or the like is appropriate, a local maximum appears in the total potential curve. Unless the kinetic energy of the fine particles is larger than the local maximum, the fine particles cannot approach to each other beyond the local maximum and aggregation is not generated, so that the system is stabilized. In contrast, in the case the electrostatic repulsion potential is changed by adsorption of counter ions, or the like, or the ionic strength increase, the local maximum value of the total potential curve is reduced, so that the particles come to be aggregated beyond the energy barrier. On the other hand, cross linking aggregation is generated due to the existence of a polymer capable of cross-linking a plurality of fine particles.

The fine particles having a dispersion property higher than that of the lyophobic fine particles refer to fine particles having the local maximum appearing in the total potential curve in the above-mentioned DLVO theory at a position with an inter particle distance wider than that shown by the local maximum position of the functional fine particles, at the start of aggregation. Or the fine particles having a dispersion property higher than that of the lyophobic fine particles refer to the fine particles having a total potential curve with a sufficiently large local maximum appearing at a position showing a sufficient inter particle distance, in a state that the local maximum of the total potential curve of the lyophobic fine particles is vanishing. Since the shape of the total potential curve is determined mainly by the Hamaker constant and the Stern electric potential value, the kinds of the lyophobic fine particles are not particularly limited by the definition.

As specific examples of the dispersible fine particles, a swellable layered silicate such as a smectite can be presented.

The reason why the swellable layered silicate is presented particularly as an example of the dispersible fine particles is that the face surface thereof is charged negatively and it continues to disperse sufficiently, even in the situation that the lyophobic fine particles are aggregated and deposited. Even in the case where it is deposited in a severer situation, it maintains a moderate aggregation form to some extent and it is re-dispersed easily by the shearing force such as the agitation Moreover, it has a small particle size so that the number of the particles existing in a dispersion is sufficient even with a slight concentration by weight, thereby covering the periphery of the lyophobic fine particles. Moreover, since the shape is plate-like, the inter particle interaction can easily be generated so that the apparent viscosity of the dispersion medium is raised, the diffusion speed of the particles is lowered, and the progress of the aggregation of the lyophobic fine particles can be prevented.

Either a synthetic one or a natural one can be used as the layered silicate, and a synthetic one is used preferably. A swellable clay mineral obtained by refining a natural one can also be used preferably. Unlike a natural one, since a synthetic one is chemically homogeneous, it contains little impurities, it has a high swelling property without containing an aggregating ion, and furthermore, it has a high transparency without including a color metal such as an iron between the layers, it is suitable for an optical measuring means.

Such a swellable layered silicate is commercially available

As the dispersion medium for the dispersion phase in the present invention, a liquid or a gas of water, alcohol, a hydrocarbon, or the like can be used, and it is not particularly limited, but water can be used preferably. At the time, the dispersion complex of the present invention is collected as a sol with water as a dispersion medium. In addition, the dispersion complex of the present invention is collected as a gel by means of drying, or the like.

The concentration of the dispersible fine particles in the present invention is not particularly limited as long as it is regarded as being sufficient for covering the periphery of the lyophobic fine particles to be controlled. Here, the concept of covering the periphery means that the number of the fine particles having a higher dispersion property exceeds drastically that of the lyophobic fine particles existing in a unit space. As a result, it may be sufficient for restraining progress of aggregation or precipitation of the lyophobic fine particles to be controlled. For example, in the case where the number concentration of the lyophobic fine particles is about $12^{th}$ power of 10 in 1,000 cc, the dispersible fine particles of $15^{th}$ power of 10 can be regarded as sufficient. As a specific example, a preferable concentration of the lyophobic fine particles necessary for execution of the analysis is 0.01 mM to 4 M, and the concentration of the dispersible fine particles necessary for covering the lyophobic fine particles in the concentration range is in general 0.1 g/L or more in the case of a swellable layered silicate. In contrast, the maximum preparing concentration of the dispersible fine particles of a swellable layered silicate is in general 250 g/L, and 300 g/L in the case of condensation. However, it is not limited thereto, and it depends on the kind and the concentration of the lyophobic fine particles, the means for starting the aggregation, and the nature of the dispersible fine particles themselves.

The dispersion state of the lyophobic fine particles can be controlled by the present invention. An example of controlling and stabilizing the lyophobic fine particles in an assembly state as in the present invention has not been known so far. Moreover, an example of stabilizing for more than one month as in the present invention has not been known neither. A dispersion complex of the lyophobic fine particles with the dispersion state controlled can be obtained by the present invention. The dispersion complex has the lyophobic fine particle assembly existing in a state preferable for providing the function, so that it is applicable to the optical element, the sensor, the catalyst, or the like.

As the analyte in the present invention, an amino acid, a base, a protein, and a nucleic acid in an aqueous solution can be presented. Moreover, an aromatic chlorine compound in the environment, or the like can be presented. However, it is not limited thereto.

As the optical measuring means in the present invention, the vibration spectroscopy such as the Raman spectroscopy and the infrared spectroscopy can be used. As the optical measuring means utilizing the surface enhancing effect, the RAS (reflection absorption spectroscopy), the SEWS (surface electromagnetic wave spectroscopy), the SEIRA (surface-enhanced infrared spectroscopy), the SERS (surface-enhanced Raman spectroscopy) the SERRS (surface-enhanced resonance Raman spectroscopy), the SEHRS (surface-enhanced hyper Raman scattering), or the like are known.

In the analysis method of the present invention, as the lyophobic fine particles, metal fine particles of gold, silver, copper, platinum, nickel, indium and palladium or semiconductor fine particles of gallium or gallium arsenide, which have been confirmed to provide the surface enhancing effect in the wavelength range used for the vibration spectroscopy, can be used preferably. In the analysis method of the present invention, as the dispersible fine particles, a synthetic smectite having a good transparency can be used preferably.

Since the dispersion complex of the present invention can work as the substrate of the surface enhancing effect for at least several month without adsorption of the metal fine particles on the pipe wall or the wall of the container in the flow system, analysis can be carried out in the flow system. In the case the dispersion complex is a sol, it can flow in the flow system as the substrate of the surface enhancing effect, can be brought into contact with the specimen solution containing the analyte, and can be measured by the optical measuring means. As an example of the flow system, a capillary electrophoresis, and various kinds of chromatographies are known.

Moreover, in the case where the dispersion complex is a gel, it can be used in contact with the specimen solution containing the analyte like a sensor. Preferably, the dispersion complex can be used as a disposable sensor. Of course the sensor may comprise a part of the flow system.

According to the dispersion complex of the present invention, by modifying the synthetic smectite with at least one substance selected from the group consisting of a ligand compound, an antibody, an antigen, an enzyme, an enzyme substrate, a nucleic acid, and a complement of a nucleic acid, the function of recognizing or orienting the analyte can be provided. In this case, since the sensitization degree of the surface enhancing effect is significantly lowered if the distance from the surface of the lyophobic fine particles is larger, a recognized substance or a part of the functional groups by the orientation can contribute to the surface enhancing effect so that it can be utilized for the selective measuring method for the substances.

BEST MODE FOR CARRYING OUT THE INVENTION

Preparation Example of a Dispersion Complex Sol

Gold fine particles were synthesized in an aqueous solution according to the chemical reduction method of adding a sodium citrate to 120 cc of a 0.6 mM aqueous chloroaurate solution so as to be 1.6 mM. As a result of measurement of the average particle size of the gold fine particles by the small angle X ray scattering method, it was about 40 nm. After measuring the absorbance of the obtained gold fine particle containing aqueous solution, it was divided into four containers, and a sodium chloride was introduced to each container as the aggregating agent so that the concentration becomes 50 mM/L and began to cause the aggregation.

Figure 1:
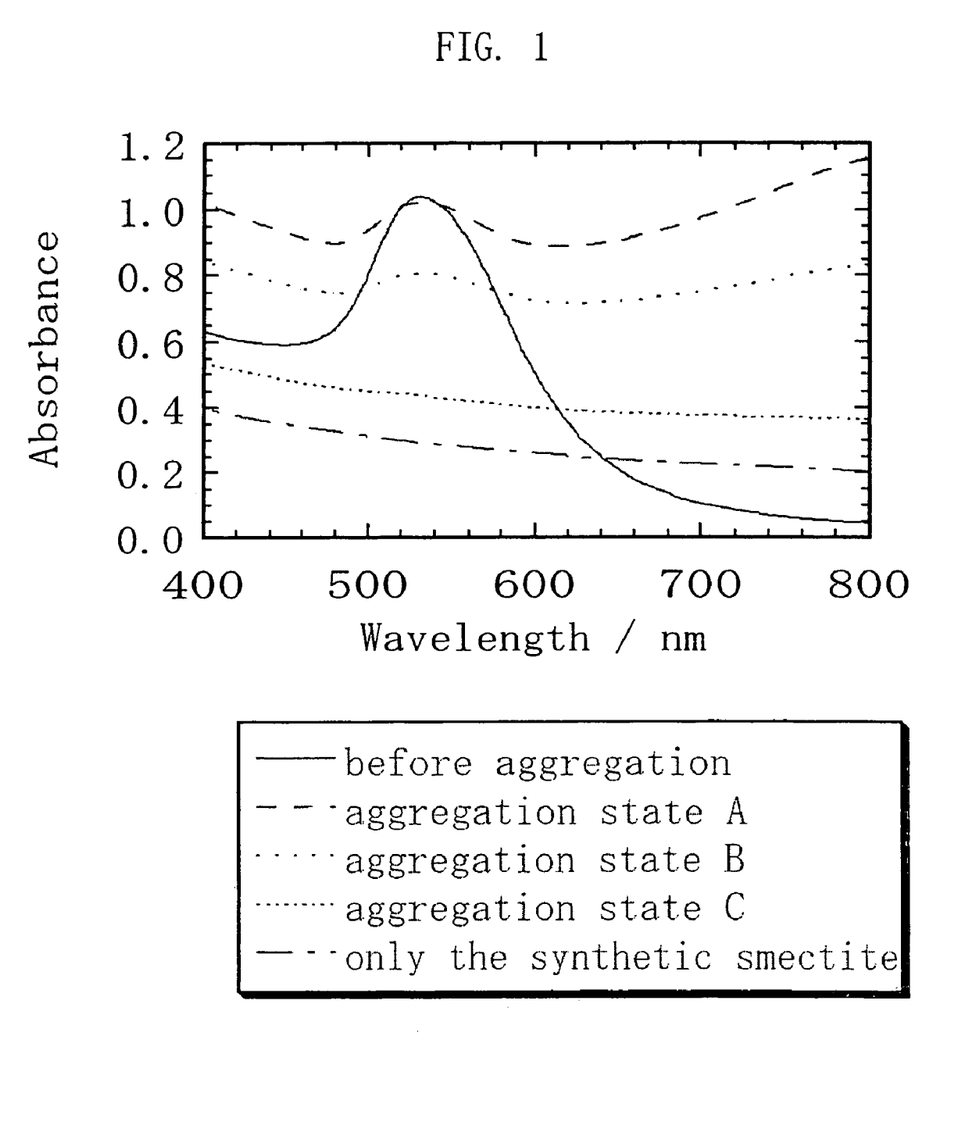
FIG. 1 shows absorption spectra of a sol containing a gold fine particle group and a synthetic smectite.

Then, in the first container, the color of the gold fine particle liquid was changed from the original red to the reddish purple, the bluish purple, the reddish brown, the brown and black, and finally it was precipitated. To the second to fourth containers, a slurry of a synthetic smectite (produced by Laporte Corp.) was added each after passage of a predetermined time. Then, the color change was stopped, so that a dispersion complex showing a different color was obtained according to the synthetic smectite addition period. The passage times from the addition of the sodium chloride to the addition of the synthetic smectite were set so as to be the second container (hereinafter, the aggregation state A)<the third container (hereinafter, the aggregation state B)<the fourth container (hereinafter, the aggregation state C). FIG. 1 shows the absorption spectra of the state before the sodium chloride addition (=before the aggregation), the aggregation state A, the aggregation state B and the aggregation state C. For the comparison, the absorbance of only the synthetic smectite was measured.

In the case the particle size is same, since the color of the gold colloid depends on the aggregation state of the particles (N. G. Khlebtsov, V. A. Bogatyrev, L. A. Dykman, and A. G. Melnikov, J. Colloid Interface Sci., 180 (2), 436-445 (1996); Spectral Extinction of Colloidal Gold and Its Biospecific Conjugates.), from the results shown in FIG. 1, it was found that a dispersion complex with the assembly state of the gold fine particles controlled can be produced according to the method of the present invention.

Stability Evaluation 1 of a Dispersion Complex Sol

Figure 2:
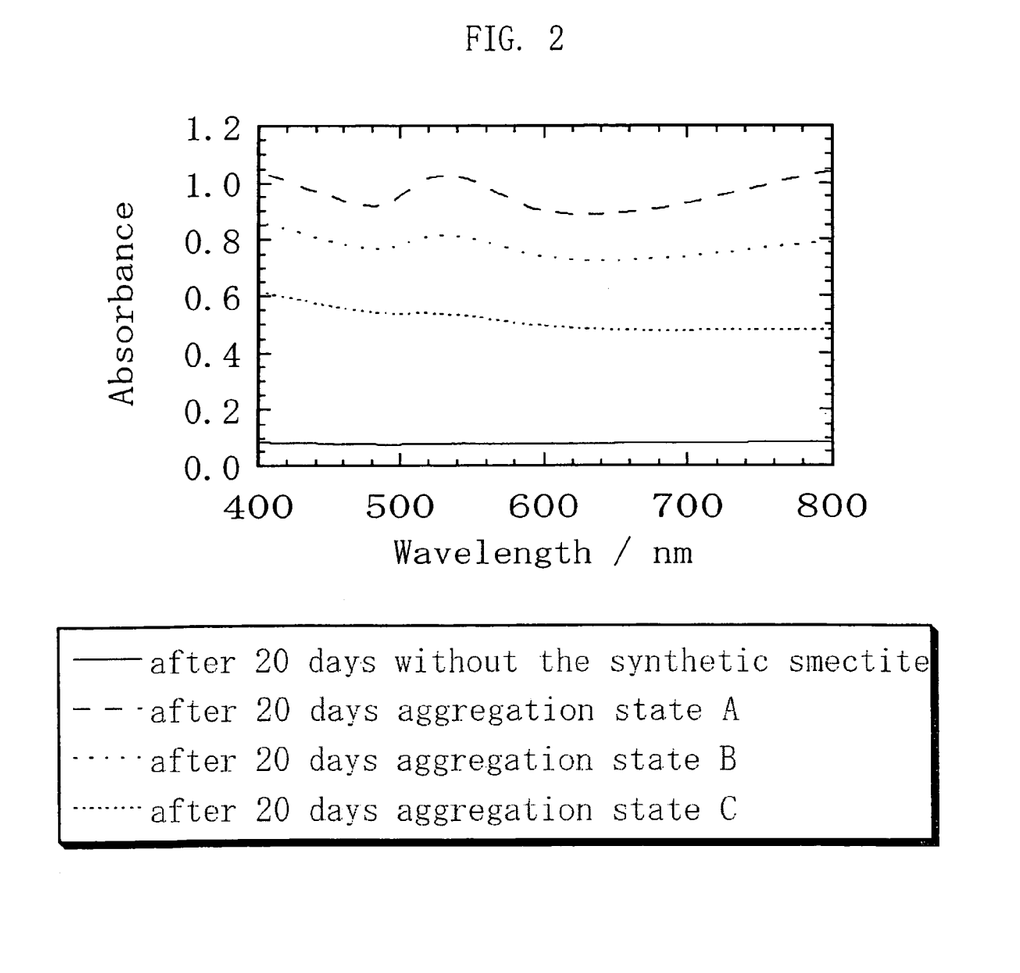
FIG. 2 shows absorption spectra of the same sol after 20 days.

The absorption spectrum of the solution in the first container in the above-mentioned preparation example, and the absorption spectra after passage of 20 days of the dispersion complexes of the aggregation states A to C are each shown in FIG. 2. As shown in FIG. 2, it was found that the dispersion complex containing the synthetic smectite maintains the state with the assembly of the gold fine particles controlled, so that it is stabilized over a long term.

Stability Evaluation 2 of a Dispersion Complex Sol

Figure 3:
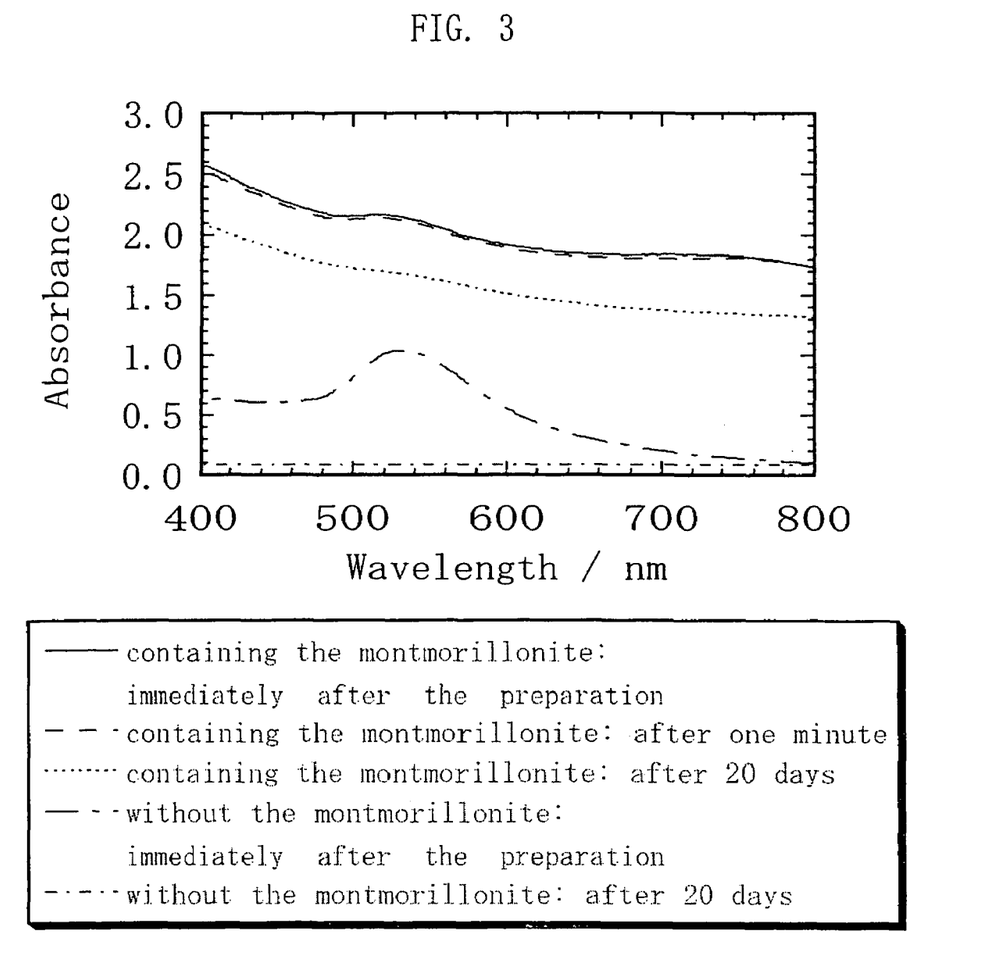
FIG. 3 shows absorption spectra of a sol containing a gold fine particle group and a montmorillonite.

A dispersion complex was prepared in the same manner as in the aggregation state A in the above-mentioned preparation example except that a montmorillonite (produced by Kunimine Kogyo Corp.) was used instead of the synthetic smectite. Although the color change was not observed for several minutes even if it was left in a room temperature, it was changed gradually to the brown over several days. However, precipitation was not generated. The absorption spectra immediately after the preparation, after one minute, and after passage of 20 days are shown in FIG. 3. As shown in FIG. 3, it was found that the dispersion complex containing the montmorillonite is stabilized while maintaining the state that the assembly of the gold fine particles are controlled.

Preparation Example of a Dispersion Complex Gel and Stability Evaluation

Figure 4:
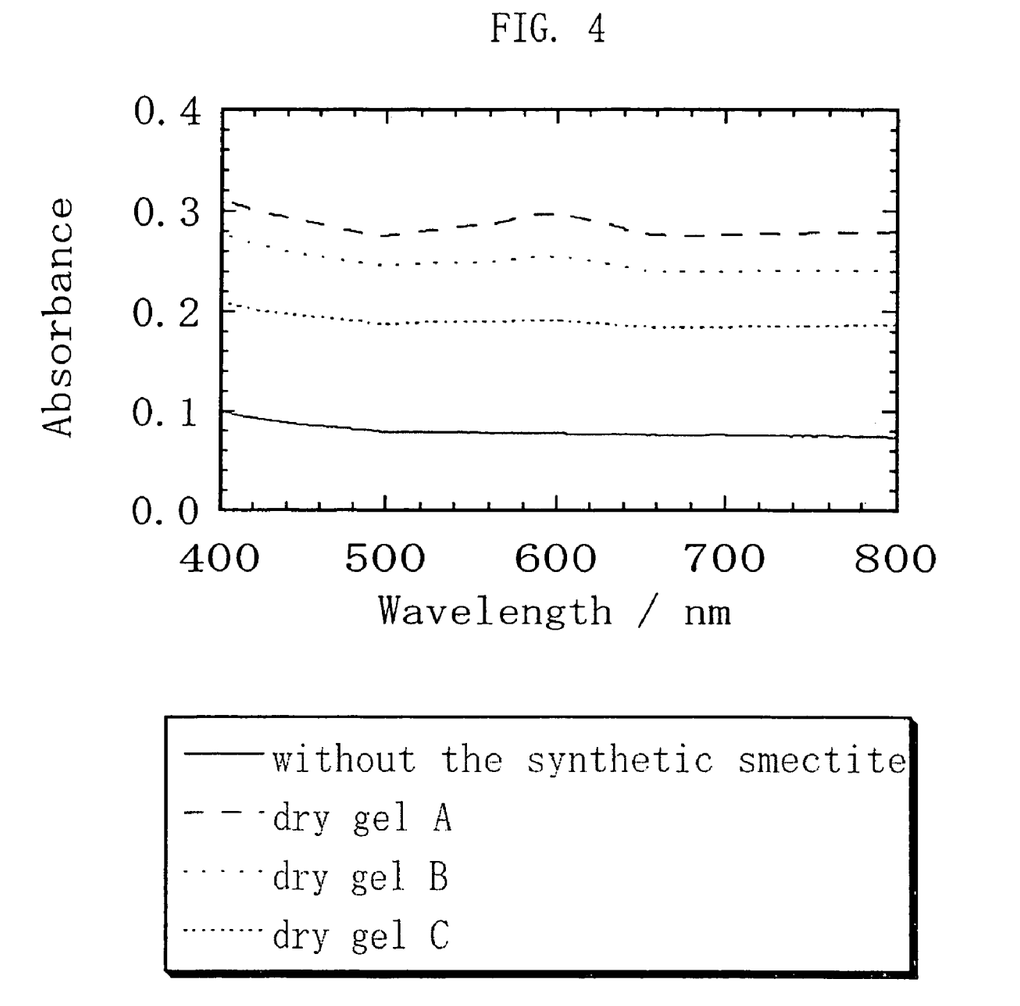
FIG. 4 shows absorption spectra of a dry gel containing a synthetic smectite and a gold fine particle group.

Polystyrene plates with the surface processed to be hydrophilic by the ultraviolet ray radiation were prepared so that the dispersion complexes of the above-mentioned aggregation states A to C were dropped onto the plates, and dried for gelation. For the comparison, a gold fine particle-containing solution not containing a synthetic smectite was dropped onto the plate in the same manner. The gels containing the synthetic smectite were spread evenly on the plates while maintaining the reddish brown or brown color. The state was stable for at least six months. In contrast, the gold fine particles derived from the solution not containing the synthetic smectite were spread unevenly on the plate as a black sediment. For the confirmation, the absorption spectra of the solid dispersion complexes obtained on the plates are shown in FIG. 4. As shown in FIG. 4, it was found that it was stabilized while maintaining the state that the assembly of the gold fine particles is controlled owing to the existence of the synthetic smectite.

EXAMPLE 1

After preparation of the dispersion complex (aggregation state B) of the above-mentioned sol preparation example, 570 µl thereof was collected, followed by mixing well with 30 µl of a 0.05 M pyridine aqueous solution, thereby obtaining a first liquid mixture. Independently thereof, 570 µl of pure water was collected, followed by mixing well with 30 µl of a 0.05 M aqueous pyridine solution, thereby obtaining a second liquid mixture. The Raman spectra of the two kinds of the liquid mixtures were measured using a Fourier transform infrared spectrophotometer "Nicolet magna 650" comprising a Raman module by a 1,064 nm excitation wavelength.

As a result, the ring breathing vibration (about 1,010 cm$^{-1}$) of a 2.5 mM pyridine was remarkably observed in the first liquid mixture. In contrast, the pyridine of the concentration was not at all observed in the second liquid mixture (ordinary Raman spectroscopy). Therefore, it was found that the above-mentioned dispersion complex can provide the substrate of the surface enhancing effect, enabling the easy analysis using the surface enhancing effect with a commercially available Raman spectroscopy device.

According to a silicic acid compound such as a smectite, in general, the Raman peak appears at:

| | |
|---|---|
| 485 cm$^{-1}$ | Si—O—Si rocking/bending of hydrated silicate |
| 809 cm$^{-1}$ | SiO2 silicate chain mode |
| 976 cm$^{-1}$ | Si—O stretch of bulk chain, | however, it didn't appear in the first liquid mixture. Therefore, it was revealed that there is no interference of the silicic acid compound. This point extremely disagrees with the conventional background report showing the Raman peak derived from a silicic acid compound in the Raman spectrum of a sol gel glass (F. Akbarian, B. S. Dunn, and J. I. Zink, J. Raman Spectrosc., 27 (10), 775-783 (1996): Porous sol-gel silicates containing gold particles as matrixes for surface-enhanced Raman spectroscopy).

EXAMPLE 2

After passage of one day after preparation of the above-mentioned dispersion complex (aggregation state B) of the above-mentioned sol preparation example, 570 µl thereof was collected, followed by mixing well with 30 µl of a 0.05 M pyridine aqueous solution, thereby obtaining a third liquid mixture. Similarly, after passage of one day after preparation of a gold fine particle aggregation liquid not containing a synthetic smectite, 570 µl thereof was collected, followed by mixing well with 30 µl of a 0.05 M pyridine aqueous solution, thereby obtaining a fourth liquid mixture. Results of measurement of the Raman spectra of the two kinds of the liquid mixtures using a Fourier transform infrared spectrophotometer "Nicolet magna 650" comprising a Raman module by a 1,064 nm excitation wavelength are shown in FIG. 5.

Figure 5:
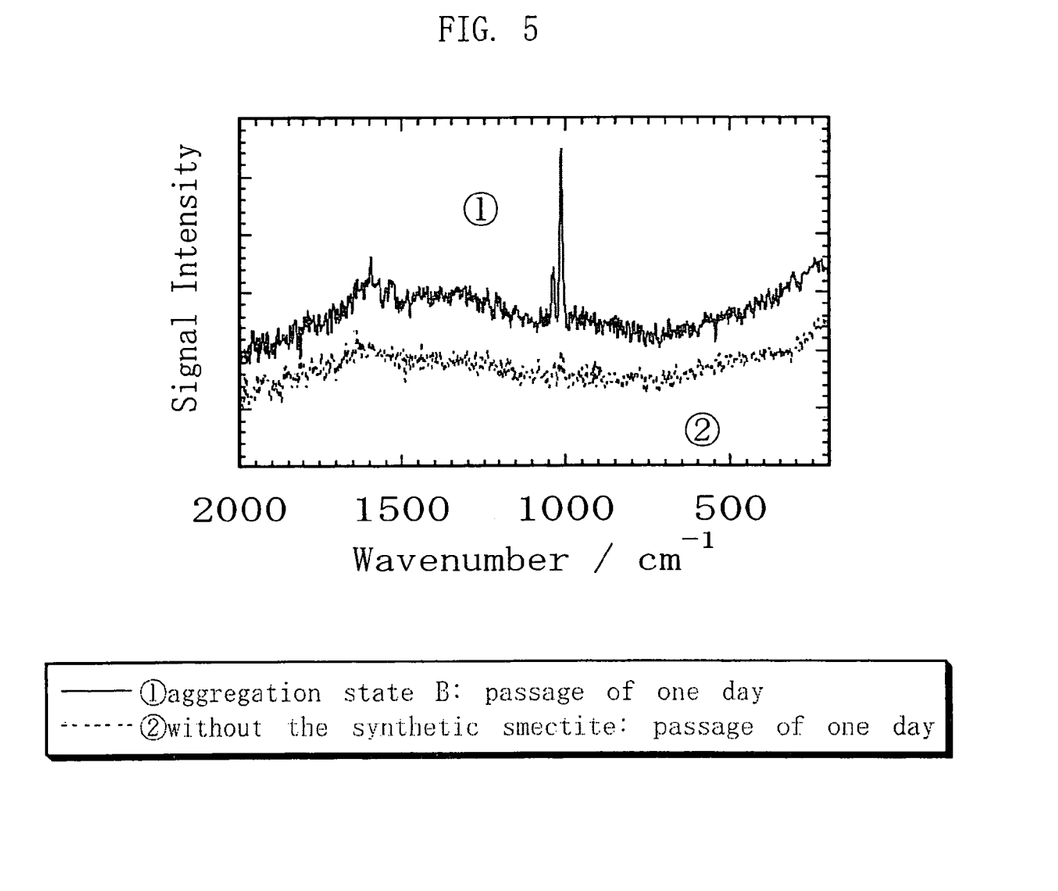
FIG. 5 shows Raman spectra containing a pyridine and a gold fine particle group.

As shown in FIG. 5, the ring breathing vibration (about 1,010 cm$^{-1}$) of a 2.5 mM low concentration pyridine was remarkably observed in the third liquid mixture containing the synthetic smectite. In contrast, it was hardly observed in the fourth liquid mixture not containing the synthetic smectite. Therefore, it was found that the above-mentioned dispersion complex is a substrate of the surface enhancing effect, enabling also after passage of one day the easy analysis using the surface enhancing effect with a commercially available Raman spectroscopy device.

EXAMPLE 3

Figure 6:
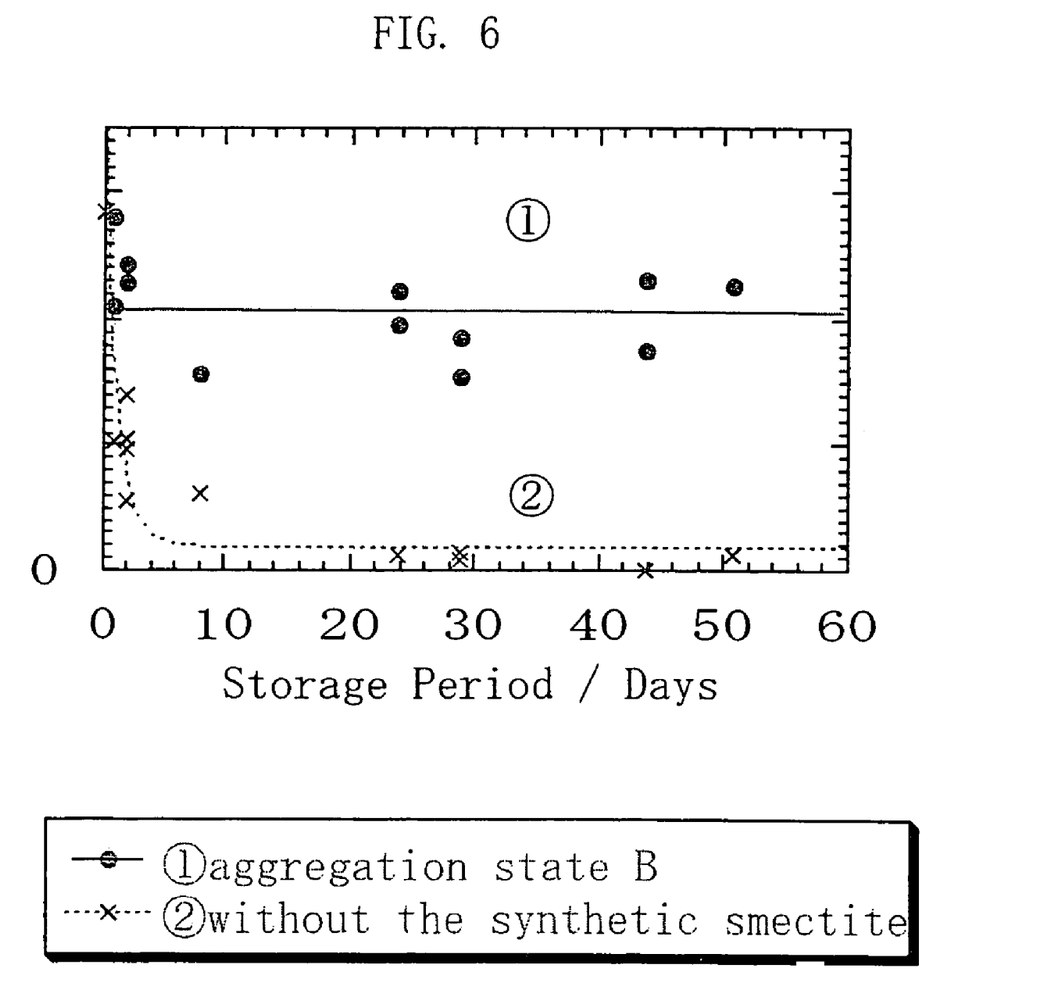
FIG. 6 shows the time passage transition of the Raman signal intensity of a sol containing a pyridine and a gold fine particle group.

The dispersion complex (aggregation state B) of the above-mentioned sol preparation example was stored at a room temperature. After passage of predetermined days, the Raman spectrum of the pyridine was measured by the method of the example 1 and, then, the transition of the ring breathing vibration signal intensity was plotted with respect to the dispersion complex storage period (● mark in the figure), thereby obtaining FIG. 6. For the comparison, the fourth liquid mixture of the example 2 (x mark in the figure) was used. As shown in FIG. 6, it was found that the above-mentioned dispersion complex works as the substrate of the surface enhancing effect over a long term of almost two month.

EXAMPLE 4

Figure 7:
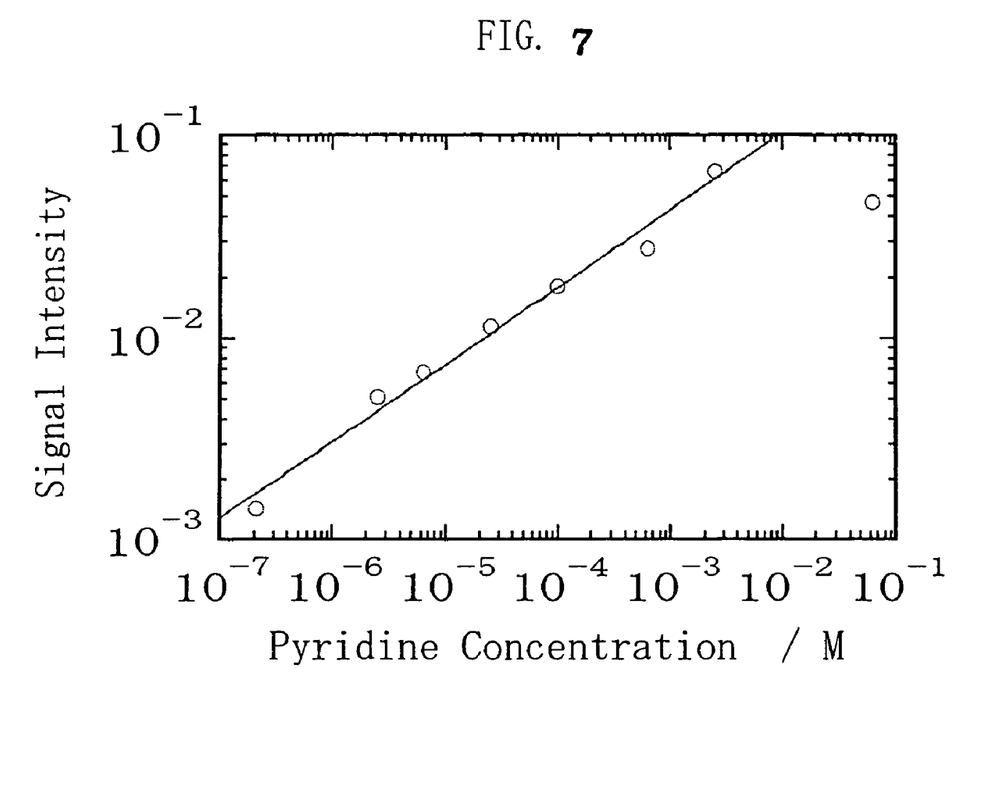
FIG. 7 is an calibration curve of an aqueous solution containing a dispersion complex and a pyridine.

Pyridine aqueous solutions having the dispersion complex of the present invention as the substrate of the surface enhancing effect were analyzed with the concentration of the aqueous pyridine solutions changed in the same manner as in the example 1. A calibration curve made from the analysis results are shown in FIG. 7. From FIG. 7, it was found that the dispersion complex according to the present invention works as the substrate of the surface enhancing effect usable for the concentration measurement.

INDUSTRIAL APPLICABILITY

As mentioned above, the substance analysis method of the present invention is effective for analysis of a slight amount substance or a low concentration substance.

The invention claimed is:

1. A method of producing a dispersion complex, comprising:
   a step of preparing a dispersion phase of lyophobic fine particles grouped by adding an aggregating agent to a liquid phase containing the lyophobic fine particles; and
   a step of making dispersible fine particles coexist in the dispersion phase at a concentration sufficient for covering a periphery of the entire group of lyophobic fine particles, the dispersible fine particles having a dispersion property higher than that of the lyophobic fine particles.

2. The method according to claim 1, wherein the lyophobic fine particles contain as a main component at least one metal selected from the group consisting of gold, silver, copper, platinum, nickel, indium and palladium.

3. The method according to claim 2, wherein the dispersible fine particles are a swellable layered silicate.

4. A dispersion complex, comprising:
   a liquid phase containing an aggregating agent;
   lyophobic fine particles existing in the liquid phase in a group; and
   dispersible fine particles coexisting in the dispersion phase at a concentration sufficient for covering a periphery of the entire group of lyophobic fine particles, the dispersible fine particles having a dispersion property higher than that of the lyophobic fine particles.

5. The dispersion complex according to claim 4, wherein the lyophobic fine particles contain as a main component at least one metal selected from the group consisting of gold, silver, copper, platinum, nickel, indium and palladium.

6. The dispersion complex according to claim 5, wherein the dispersible fine particles are a swellable layered silicate.

* * * * *